United States Patent [19]

Edwards

[11] 4,297,124
[45] Oct. 27, 1981

[54] N-TETRACHLORO-ETHYLTHIO-SUBSTITUTED HALOMETHANESULFONAMIDES AS AQUATIC WEED CONTROL AGENTS

[75] Inventor: Laroy H. Edwards, Napa, Calif.

[73] Assignee: Chevron Research Company, San Francisco, Calif.

[21] Appl. No.: 115,586

[22] Filed: Jan. 28, 1980

[51] Int. Cl.³ .................................................. A01N 31/02
[52] U.S. Cl. ............................................ 71/66; 71/67; 71/103; 71/98
[58] Field of Search .................. 71/67, 98, 103, 66; 260/453 RW; 424/321

[56] References Cited

U.S. PATENT DOCUMENTS

| | | | |
|---|---|---|---|
| 3,574,767 | 4/1971 | Kohn | 71/67 |
| 3,679,673 | 7/1972 | Brown | 71/67 |
| 3,734,710 | 5/1973 | Lukaszczyk et al. | 71/103 |
| 3,784,649 | 1/1974 | Buckman et al. | 71/67 |
| 3,839,349 | 10/1974 | Wagner et al. | 71/67 |
| 3,843,792 | 10/1974 | Brown | 71/67 |
| 4,068,000 | 1/1978 | Edwards | 424/321 |

*Primary Examiner*—Glennon H. Hollrah
*Attorney, Agent, or Firm*—J. A. Buchanan, Jr.; T. G. DeJonghe; L. S. Squires

[57] ABSTRACT

N-tetrachloroethylthio-substituted halomethanesulfonamides of the formula

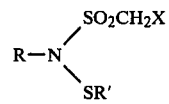

wherein R is alkyl, cycloalkyl, acyl, X is fluoro, chloro, bromo or iodo and R' is tetrachloroethyl, are useful as algicides.

2 Claims, No Drawings

N-TETRACHLORO-ETHYLTHIO-SUBSTITUTED HALOMETHANESULFONAMIDES AS AQUATIC WEED CONTROL AGENTS

BACKGROUND OF THE INVENTION

U.S. Pat. No. 3,178,447, issued to G. K. Kohn on Apr. 13, 1965, discloses the fungicidal activity of N-polyhaloethylthio-substituted aryl- and alkanesulfonamides.

U.S. Pat. No. 2,779,788, issued to H. Gysin et al on Jan. 29, 1957, discloses fungicidal N-trichloromethylthio-substituted chloromethanesulfonamides.

U.S. Pat. No. 3,925,555, issued to I. Okuda et al on Dec. 9, 1975, discloses the control of mites with chloromethanesulfonamides.

In my commonly assigned U.S. Pat. No. 4,068,000 I disclose miticial and mite ovicidal N-tetrachloroethylthio-substituted halomethanesulfonamides.

DESCRIPTION OF THE INVENTION

In U.S. Pat. No. 4,068,000 I describe mite ovicidal compounds represented by the formula

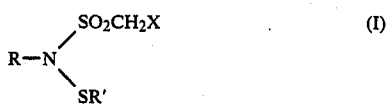

(I)

wherein R is alkyl of 1 to 8 carbon atoms, cycloalkyl of 5 to 8 carbon atoms substituted with up to 2 alkyl of 1 to 3 carbon atoms, phenyl substituted with up to 2 fluoro, chloro, bromo, iodo or alkyl of 1 to 4 carbon atoms; X is fluoro, chloro, bromo or iodo and R' is tetrachloroethyl.

I have now discovered that these compounds are useful as algicides, particularly for control of algae and slime in large aqueous bodies, such as lakes, streams and pools, and in aqueous industrial effluents and cooling streams.

Representative R groups include alkyl such as methyl, ethyl, isopropyl, sec-butyl and hexyl; cycloalkyl and alkylcycloalkyl such as cyclopentyl, 2-methylcycloalkyl, 3-methylcyclohexyl, 3,5-dimethylcycloheptyl and cyclooctyl; and aryl groups such as phenyl, 2-fluorophenyl, 3-chlorophenyl, 4-bromophenyl, 4-iodophenyl, 4-methylphenyl and 2-chloro-4-methylphenyl. Tetrachloroethyl $R^1$ groups are 1,1,2,2-tetrachloroethyl and 1,2,2,2-tetrachloroethyl.

Preferred R groups are alkyl, especially alkyl of 1 to 4 carbon atoms and cycloalkyl of 5 to 6 carbon atoms substituted with up to 1 alkyl of 1 to 3 carbon atoms. The preferred X groups are chloro or bromo. The preferred R' group is 1,1,2,2-tetrachloroethyl.

Representative compounds of formula (I) include N-cyclopentyl-N-(1,1,2,2-tetrachloroethylthio)-chloromethanesulfonamide, N-cycloheptyl-N-(1,1,2,2,-tetrachloroethylthio)-bromomethanesulfonamide, N-(2-fluorophenyl)-N-(1,1,2,2-tetrachloroethylthio)-iodomethanesulfonamide, N-(4-chlorophenyl)-1,1,2,2-tetrachloroethylthio)-bromomethanesulfonamide, N-(3-iodophenyl)-N-(1,1,2,2-tetrachloroethylthio)-iodomethanesulfonamide, N-cyclohexyl-N-(1,2,2,2-tetrachloroethylthio)-bromomethanesulfonamide, N-phenyl-N-(1,2,2,2-tetrachloroethylthio)-chloromethanesulfonamide, N-isopropyl-N-(1,2,2,2,-tetrachloroethylthio)-fluoromethanesulfonamide, and N-(2,4-dichlorophenyl)-N-(1,2,2,2-tetrachloroethylthio)-chloromethanesulfonamide.

The compounds of the invention are prepared by sulfenylating a sulfonamide of the formula R NHSO$_2$CH$_2$X (II), wherein R and X have same significance as previously defined, with a tetrachloroethylsulfenyl halide, e.g., 1,1,2,2,-tetrachloroethylsulfenyl chloride or 1,2,2,2-tetrachloroethylsulfenyl chloride. The sulfenylation reaction is conducted by reacting substantially equimolar quantities of the sulfonamide (II) and the sulfenyl halide in the liquid phase in the presence of a base. Suitable bases are organic amines such as pyridine compounds, e.g., pyridine or alphapicoline, and lower trialkylamines, e.g., triethylamine or tributylamine, and inorganic alkali metal hydroxides, e.g., sodium hydroxide or potassium hydroxide. Generally, at least one mol of base is employed for each mol of tetrachloroethylsulfenyl halide. The reaction is normally conducted in an inert liquid diluent, e.g., organic solvents such as chlorinated hydrocarbons.

Preferably, the reaction is conducted in the presence of catalytic amounts of a quaternary ammonium salt. Generally, amounts of quaternary ammonium salt per mol of the sulfenyl halide reactant vary from about 0.01 to 0.3, although amounts from 0.05 to 0.2 mol per mol of the sulfenyl halide are preferred. Suitable quaternary ammonium salts are tetraalkylammonium halides wherein the alkyl has 1 to 6 carbon atoms and the halide is fluoro, chloro, bromo or iodo, e.g., tetramethaneammonium chloride or tetrabutylammonium bromide.

The sulfenylation reaction is conducted at a temperature of 0° C. to the boiling point of the diluent, although temperatures between 0° C. and 100° C. are preferred. The reaction is conducted at or above atmospheric pressure. The reaction time will, of course, vary depending on the reaction temperature and the particular reactants employed. Generally, the reaction is completed within one-half to 24 hours. The product (I) is isolated and purified by conventional procedures such as extraction, filtration, crystallization and chromatography.

The compounds of the invention are useful for controlling microbiological organisms such as algae, bacteria, molds, slime and occasionally aquatic weeds which foul aqueous industrial effluents and cooling streams, such as those occurring in the paper and food processing industries. They may also be used to control such organisms in other aqueous bodies such as lakes, streams, canals, pools and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water one foot deep 0.1 to 10 ppm is equal to about 0.3 to 30 pounds per acre of water one foot deep. These compounds may be applied to the aqueous growth environments of such organisms as dispersible powders or in solution with water-miscible solvents.

EXAMPLE 1

Aquatic Plant and Algae Control

Representative compounds of the invention were tested as algicides by the following method. The aquatic test species were *Lemna, Elodea* and *Spirulina*. An acetone solution of the test compound and a small amount of an alkylarylpolyoxyethylene glycol-containing surfactant was prepared. This solution was mixed with a nutrient solution in a quantity sufficient to give a concentration of 2 ppm. This mixture was placed in a clear 240 ml container. Samples of the test species were added to each container and the container was then placed in an illuminated environment and maintained at a temperature of about 20° C. for incubation. The containers were observed periodically for growth (as compared to an untreated check). The effectiveness of the test compound was determined based on a final observation of growth after 7 to 10 days. The results of the test on a 0 to 100 basis—0 indicating no effectiveness and 100 indicating complete effectiveness—are reported in Table I.

dichloromethane. The reaction was then allowed to warm to about 25° C. and stirred about 16 hours. The reaction mixture was then filtered, washed with water, dried over magnesium sulfate and evaporated to give 22.0 g of crude N-cyclohexyl bromomethanesulfonamide.

A 5.1 g (0.051 mol) sample of triethylamine was added dropwise to a cooled (20° C.) solution of 11 g (0.043 mol) N-cyclohexylbromomethanesulfonamide and 10.1 g (0.043 mol) 1,1,2,2-tetrachloroethylsulfenyl chloride. After the addition was completed, the reaction was stirred at ambient temperature for 2 hours and then under reflux for 2 hours. The reaction mixture was then cooled, washed with water, dried over magnesium sulfate and evaporated under reduced pressure to give the N-cyclohexyl-N-(1,1,2,2-tetrachloroethylthio)-bromomethanesulfonamide product, which after crystallization from dioxane melted at 38°–40° C. The elemental analysis for the product is tabulated in Table I under Compound No. 8.

EXAMPLE 3

TABLE I

Compound of the formula

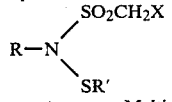

| Compound No. | R | R' | X | Melting Point °C. | % Control Spiru, | Lem. | Elod. |
|---|---|---|---|---|---|---|---|
| 1 | i-C$_3$H$_7$ | CCl$_2$CCl$_2$H | Cl | 78–80 | — | 0 | 0 |
| 2 | cyclohexyl | " | Cl | 73–74 | — | 0 | 0 |
| 3 | CH$_3$ | " | Cl | Oil | — | 100 | 100 |
| 4 | φ | " | Cl | 91–92 | — | 78 | 78 |
| 5 | s-C$_4$H$_9$ | " | Cl | Oil | — | 50 | 90 |
| 6 | cyclopentyl | " | Cl | 67–68 | — | 100 | 94 |
| 7 | 4-CH$_3$—cyclohexyl | " | Cl | 63–65 | — | 0 | 60 |
| 8 | cyclohexyl | " | Br | 38–40 | 40 | 0 | 15 |
| 9 | cyclopentyl | " | Br | 59–60 | 70 | 78 | 70 |
| 10 | s-C$_4$H$_9$ | " | Br | Oil | 30 | 0 | 0 |
| 11 | 4-CH$_3$—cyclohexyl | " | Br | Oil | 0 | 0 | 0 |
| 12 | cyclooctyl | " | Br | Oil | 0 | 0 | 0 |
| 13 | φ | " | Br | 101–103 | 0 | 30 | 0 |
| 14 | CH$_3$ | " | Br | Oil | 50 | 96 | 0 |
| 15 | n-C$_3$H$_7$ | " | Br | Oil | 0 | 99 | 90 |
| 16 | i-C$_3$H$_7$ | " | Br | 75–77 | 0 | 39 | 39 |
| 17 | n-C$_4$H$_9$ | " | Br | Oil | 0 | 39 | 39 |
| 18 | t-C$_4$H$_9$ | " | Br | 78–80 | 0 | 30 | 39 |
| 19 | p-tolyl | " | Br | 100–103 | 0 | 22 | 30 |
| 20 | i-C$_3$H$_7$ | CCl$_3$ | Cl | 78–80 | — | 0 | 0 |
| 21 | cyclohexyl | " | Cl | 108–109 | — | 0 | 0 |
| 22 | CH$_3$ | " | Cl | 70–72 | — | 0 | 0 |
| 23 | cyclooctyl | " | Cl | Oil | — | 0 | 0 |
| 24 | φ | " | Cl | 115–117 | — | 0 | 0 |
| 25 | s-C$_4$H$_9$ | " | Cl | 72–74 | — | 0 | 0 |
| 26 | cyclopentyl | " | Cl | 58–60 | — | 0 | 0 |
| 27 | 4-CH$_3$—cyclohexyl | " | Cl | 87–89 | — | 0 | 0 |
| 28 | cyclohexyl | " | Br | 110–111 | 0 | 0 | 0 |
| 29 | cyclopentyl | " | Br | 70–71 | 0 | 0 | 0 |
| 30 | s-C$_4$H$_9$ | " | Br | 71–72 | 0 | 0 | 0 |
| 31 | 4-CH$_3$—cyclohexyl | " | Br | 56–57 | 0 | 0 | 0 |
| 32 | cyclooctyl | " | Br | Oil | 0 | 0 | 0 |
| 33 | φ | " | Br | 134–135 | 0 | 0 | 0 |
| 34 | p-tolyl | " | Br | 113–115 | 30 | 0 | 0 |

EXAMPLE 2

Preparation of N-cyclohexyl-N-(1,1,2,2-tetrachloroethylthio)-bromomethanesulfonamide A 20 g (0.2 mol) sample of cyclohexylamine was added dropwise to a cooled (−60° C.) solution of 23.8 g (0.1 mol) bromomethanesulfenyl bromide in 200 ml

Preparation of N-cyclopentyl-N (1,1,2,2-tetrachloroethylthio)-bromomethanesulfonamide A 5.76 g (0.072 mol) 50% aqueous solution of sodium hydroxide was added slowly to a solution of 8.6 g (0.036 mol) N-cyclopentyl bromomethanesulfonamide, 8.6 g (0.036 mol) 1,1,2,2-tetrachloroethylsulfenyl chloride, and about 0.1 g benzyltriethyl ammonium chloride in 200 mol dichloromethane cooled to 0° C. with an ice bath. The reaction mixture was then stirred at 0° C. for 2 hours, washed with water, dried over magnesium sulfate and evaporated to give a brown oil. The oil was chromatographed over silica gel with dichloromethane/petroleum-ether solution to give 5.5 g (35% yield) of the product, as a grey solid, m.p. 59°-60° C. The elemental analysis for the product is tabulated in Table I under Compound No. 9.

What is claimed is:

1. A method for controlling the growth of aquatic weeds comprising applying to said aquatic weeds or their growth environment an amount of the compound of the formula

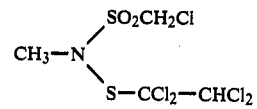

effective to control the growth of said aquatic weeds.

2. A method according to claim 1 wherein said aquatic weeds are *Elodea* or *Lemna*.